United States Patent [19]

Wada

[11] Patent Number: 4,476,317

[45] Date of Patent: Oct. 9, 1984

[54] PROCESS FOR THE PRODUCTION OF METHYLENEDICARBANILATES

[75] Inventor: Keisuke Wada, Kanagawa, Japan

[73] Assignee: Mitsubishi Chemical Industries Limited, Tokyo, Japan

[21] Appl. No.: 458,410

[22] Filed: Jan. 17, 1983

Related U.S. Application Data

[63] Continuation of Ser. No. 192,979, Oct. 1, 1980.

[30] Foreign Application Priority Data

Oct. 1, 1979 [JP] Japan .................. 54-126579
Oct. 15, 1979 [JP] Japan .................. 54-132699
Oct. 15, 1979 [JP] Japan .................. 54-132700

[51] Int. Cl.³ .......................................... C07C 125/07
[52] U.S. Cl. .................................................... 560/025
[58] Field of Search ............................................ 560/25

[56] References Cited

U.S. PATENT DOCUMENTS

| | | | |
|---|---|---|---|
| T994,004 | 5/1980 | Shawl | 560/25 |
| 2,946,768 | 7/1960 | Klauke et al. | 560/25 |
| 4,162,362 | 7/1979 | Shawl | 560/25 |
| 4,163,019 | 7/1979 | Mango | 560/24 |
| 4,230,877 | 10/1980 | Shawl et al. | 560/25 |
| 4,243,815 | 1/1981 | Merger et al. | 560/25 |
| 4,282,370 | 8/1981 | Merger et al. | 560/25 |
| 4,319,018 | 3/1982 | Miyata et al. | 560/25 X |

OTHER PUBLICATIONS

Rohm & Haas Co., "Amberlite 200", Philadelphia 5, PA, 1E-51-60(a), 4/1962.

*Primary Examiner*—Bernard Helfin
*Attorney, Agent, or Firm*—Sughrue, Mion, Zinn, Macpeak & Seas

[57] ABSTRACT

A process is described for producing methylenedicarbanilates by reacting carbanilates with formaldehyde in the presence of a specific catalyst. The catalyst is selected from (1) a cation exchanger containing sulfonic acid groups which has a proton exchange capacity of at least 0.1 meq/g, (2) a clay having an acidity of at least 0.1 meq/g at an acidic site, the acid strength of the acidic site being $-3.0$ or less as a value of acidity function $H_o$, (3) a mixed oxide having an acidity of at least 0.1 meq/g at an acidic site, the acid strength of the acidic site being $-3.0$ or less as a value of acidity function $H_o$, (4) heteropolymolybdic acid, and (5) heteropolytungstic acid.

13 Claims, No Drawings

PROCESS FOR THE PRODUCTION OF METHYLENEDICARBANILATES

CROSS REFERENCE TO RELATED APPLICATIONS

This application is a continuation of Ser. No. 192,979, filed Oct. 1, 1980.

BACKGROUND OF THE INVENTION

1. Field of the Invention

This invention relates to a process for the production of methylenedicarbanilates. More particularly, this invention provides a process for the production of methylenedicarbanilates; i.e., an intermediate product for use in the production of 4,4'-diphenylmethanediisocyanate which is generally called "MDI" and an important starting material for the production of polyurethanes.

2. Description of the Prior Art

MDI is used as a starting material for the production of polyurethane elastomers, elastic fibers, adhesives, coating resins, etc., and recently its production has been sharply increasing. At present, MDI is produced by a method which comprises reacting aniline with formaldehyde to give 4,4'-diaminodiphenylmethane and reacting the 4,4'-diaminodiphenylmethane with phosgene. This method, however, has the disadvantages in that the use of harmful phosgene is necessary, the phosgenation step is complicated, and that hydrochloric acid by-produced in the phosgenation step must be disposed of safely.

In addition to the phosgenation process, various methods have been proposed for the production of isocyanates, including: (1) a method in which aromatic carbamates are produced by reacting aromatic nitro compounds with carbon monoxide and alcohol in the presence of a catalyst comprising palladium, Lewis acid, e.g., iron chloride, and a heterocyclic base, e.g., pyridine [see Japanese Patent Application (OPI) No. 98240/1976 (The term "OPI" as used herein refers to a "published unexamined Japanese patent application")] and then decomposed by heating; (2) a method in which the same reaction is carried out in the presence of a catalyst comprising palladium, vanadyl chloride and a heterocyclic base [see Japanese Patent Application (OPI) No. 22339/1979], and a method in which the same reaction is carried out in the presence of a catalyst comprising selenium, sulfur and a base [see Japanese Patent Application (OPI) No. 62420/1974].

SUMMARY OF THE INVENTION

As a result of extensive investigations to produce methylenedicarbanilates by employing as a starting material the carbanilates which are advantageously obtained by the above described methods, it has now been found that methylenedicarbanilates can commercially advantageously be produced by reacting carbanilates with at least one selected from the group consisting of formaldehyde, oligomers of formaldehyde, acetals of formaldehyde, acylals of formaldehyde and oxymethylenebiscarboxylates in the presence of at least one acid catalyst selected from the group consisting of: (1) a cation exchanger containing sulfonic groups which has a proton exchange capacity of at least 0.1 meq/g, (2) a clay having an acidity of at least 0.1 meq/g at an acidic site, the acid strength of the acidic site being −3.0 or less as a value of acidity function H$_o$, (3) a mixed oxide having an acidity of at least 0.1 meq/g at an acidic site, the acid strength of the acidic site being −3.0 or less as a value of the acidity function H$_o$, (4) heteropolymolybdic acid and (5) heteropolytungstic acid.

This invention, therefore, provides a process for producing methylenedicarbanilates which comprises reacting carbanilates with at least one selected from the group consisting of formaldehyde, oligomers of formaldehyde, acetals of formaldehyde, acylals of formaldehyde and oxymethylenebiscarboxylates in the presence of at least one acid catalyst selected from the group consisting of: (1) a cation exchanger containing sulfonic groups which has a proton exchange capacity of at least 0.1 meq/g, (2) a clay having an acidity of at least 0.1 meq/g at an acidic site, the acid strength of the acidic site being −3.0 or less as a value of acidity function H$_o$, (3) a mixed oxide having an acidity of at least 0.1 meq/g at an acidic site, the acid strength of the acidic site being −3.0 or less as a value of acidity function H$_o$, (4) heteropolymolybdic acid and (5) heteropolytungstic acid.

DETAILED DESCRIPTION OF THE INVENTION

Carbanilates used as a starting material in this invention can be represented by the general formula:

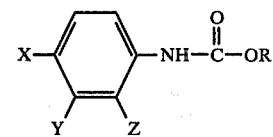

wherein R is an alkyl group containing from 1 to 4 carbon atoms or a phenyl group, and X, Y and Z are each hydrogen, a halogen atom, a nitro group, an alkyl group containing from 1 to 5 carbon atoms, an alkoxy group containing from 1 to 5 carbon atoms, or an alkoxycarbamoylphenylmethyl group wherein the alkoxy portion contains 1 to 4 carbon atoms. In particular, methylcarbanilate, ethylcarbanilate, phenylcarbanilate, 2,4'-methylenebis(ethylcarbanilate), 4,4'-methylenebis(ethylcarbanilate), etc. are preferably used. These carbanilates can be used alone or in combination with each other.

The formaldehyde may be used in various forms, such as a gaseous form or as an aqueous solution. While the formaldehyde can be used as an aqueous solution, it is preferred to reduce the amount of water in the starting material since the condensation reaction of this invention is a dehydration reaction and the reaction rate is larger as the concentration of water in the reaction system is smaller. Additionally, oligomers of formaldehyde, e.g, trioxane, paraformaldehyde, etc., acetals of formaldehyde, e.g., methylal, etc., acylals of formaldehyde, i.e., reaction products of formaldehyde and aliphatic carboxylic acids, e.g., methylidene diacetate, and oxymethylenebiscarboxylates can be used. Hereinafter, the above-mentioned compounds (including formaldehyde) are referred to as "formaldehyde compounds".

While the ratio of formaldehyde compounds to carbanilate is not critical, when the reaction rate, selectivity of the desired product, amounts of high boiling point by-products being formed, etc. are taken into account, it is generally preferred that the carbanilate is used in an amount of at least 2 moles per mole of formaldehyde compounds (converted to a formaldehyde basis), with the range of from about 3 to 10 moles being particularly preferred.

Although the process of this invention can be carried out without solvents, it is desirable to use solvents which are inert to the reaction, in order for the reaction to smoothly proceed. Solvents which can be suitably used in this invention include alkanes such as pentane, hexane, octane, etc., cycloalkanes such as coclohexane, etc., aromatic hydrocarbons such as benzene, toluene, xylene, ethylbenzene, etc., ethers such as tetrahydrofuran, dioxane, diphenyl ether, etc., ketones such as acetone, ethyl methyl ketone, cyclohexanone, etc., alkanols such as methanol, ethanol, butanol, octanol, etc., aliphatic carboxylic acids such as acetic acid, propionic acid, etc., aliphatic carboxylic acid esters such as ethyl acetate, etc., nitroalkanes such as nitromethane, etc., aromatic nitro compounds such as nitrobenzene, nitrotoluene, dinitrotoluene, etc., halogenated alkanes such as dichloromethane, dichloroethane, trichloroethane, etc., aromatic halogenated compounds such as chlorobenzene, dichlorobenzene, etc., nitriles such as acetonitrile, benzonitrile, tolunitrile, etc., amides such as N,N-dimethylformamide, N,N-dimethylacetoamide, etc., sulfoxides such as dimethylsulfoxide, etc., and cyclic sulfones such as tetrahydrothiophen-1,1-dioxide, etc.

Representative examples of cation exchangers containing sulfonic acid groups which have a proton exchange capacity of at least 0.1 meq/g include a styrene-divinylbenzene copolymer, a phenol-formaldehyde copolymer, a perfluoroethylene polymer into which a sulfonic acid functional group or groups are introduced, sulfonated coal, a sulfonated polyphenyl, a sulfonated polyphenylene oxide, a sulfonated cellulose, ect. Of these cation exchangers containing sulfonic acid groups, examples of such cation exchangers available on the market are listed in Table 1.

TABLE 1

| Cation Exchangers Containing Sulfonic Acid Groups | Trade Name | Manufacturer |
|---|---|---|
| Sulfonated styrene-divinylbenzene copolymer | Diaion SK 106 | Mitsubishi Chemical Industry Ltd. |
| | Diaion HPK 25 | Mitsubishi Chemical Industry Ltd. |
| | Amberlite 200 | Rohm & Haas Co. |
| | Amberlyst 15 | Rohm & Haas Co. |
| | Dowex 70 | Dow Chemical Co. |
| Sulfonated perfluoroethylene polymer | Nafion 501 | Dupont Co. |
| Sulfonated phenol-formaldehyde polymer | Duolite C-10 | Diamond Shamrock Corp. |
| Sulfonated coal | Permutit H-53 | Permutit A.G. |
| Sulfonated cellulose | Celex SE | Biolad Co. |

Almost all of the above cation exchangers containing sulfonic acid groups which are available on the market have a proton exchange capacity of from 1 to 10 meq/g. Since the use of those cation exchangers having small proton exchange capacities generally lowers the reaction rate, it is desirable to use cation exchangers having sulfonic acid groups which have as high a proton exchange capacity as possible.

As a typical cation exchanger containing sulfonic acid groups, a styrene-divinylbenzene copolymer with sulfonic acid functional groups introduced therein is known. A styrene-divinylbenzene copolymer cross-linked with from 2 to 18% by weight of divinylbenzene is generally available on the market. Particularly preferred are those which are generally referred to high porous or macroreticular type cation exchangers containing sulfonic acid groups, e.g., Diaion HPK 25, Amberlite 200, Amberlyst 15, Dowex 70, etc., as illustrated in Table 1. These cation exchangers give good results.

A clay or mixed oxide having an acidity of at least 0.1 meq/g at an acidic site, the acid strength of the acidic site being $-3.0$ or less as a value of acidity function $H_o$, can also be used as a catalyst of this invention. The value of acidity function of $H_o = -3.0$ corresponds approximately to an acidity of 48% by weight sulfuric acid.

As such a clay, natural or synthetic clays such as kaolinite, attapulgite, chlorite, Fuller's earth, bentonite, montmorillonite, halloysite, smectite, illite, vermiculite, sepiolite, mordenite, zeolite, etc. can be used. These clays have a cation exchange capability, and in order to further increase this activity, they are preferably subjected to protonation by treatment with an inorganic acid, e.g., hydrofluoric acid, hydrochloric acid, perchloric acid, sulfuric acid, etc., or by thermally decomposing an ammonium salt of the clay.

Examples of mixed oxides which can be used in this invention are shown in Table 2 together with their $H_o$ values.

TABLE 2

| Mixed Oxide | $H_o$ Value |
|---|---|
| $ZrO_2$—$CdO$ | ca. $-3.0$ |
| $SiO_2$—$ZnO$ | " |
| $TiO_2$—$CdO$ | " |
| $TiO_2$—$ZnO$ | " |
| $TiO_2$—$SnO$ | " |
| $SiO_2$—$La_2O_3$ | ca. $-4.0$ |
| $ZrO_2$—$Al_2O_3$ | ca. $-5.7$ |
| $TiO_2$—$Al_2O_3$ | ca. $-5.7$ |
| $SiO_2$—$Y_2O_3$ | " |
| $SiO_2$—$Ga_2O_3$ | ca. $-7.0$ |
| $TiO_2$—$ZrO_2$ | ca. $-8.2$ |
| $SiO_2$—$Al_2O_3$ | " |
| $SiO_2$—$ZrO_2$ | " |
| $SiO_2$—$TiO_2$ | " |

Heteropolymolybdic acid or heteropolytungstic acid are formed by the polycondensation of molybdic acid anion ($MoO_4^{2-}$) or tungstic acid anion ($WO_4^{2-}$) with oxyacid anion, e.g., phosphoric acid anion ($PO_4^{3-}$), silicic acid anion ($SiO_4^{2-}$), chromic acid anion ($CrO_4^{2-}$), etc. As the central element, there can be mentioned, in addition to phosphorus, silicon and chromium, titanium, zirconium, vanadium, manganese, iron, cobalt, nickel, rhodium, platinum, copper, aluminum, gallium, germanium, tin, arsenic, selenium, tellurium, iodine, cerium, thorium and the like.

Examples of heteropolymolybdic acids are $H_3Mo_{12}PO_{40}$, $H_4Mo_{12}TiO_{40}$, $H_8Mo_{12}CeO_{42}$, $H_8Mo_{11}GeO_{39}$, $H_6Mo_9MnO_{32}$, $H_5Mo_6IO_{24}$, $H_9Mo_6CrO_{24}$, $H_6Mo_{18}As_2O_{62}$, etc. Examples of heteropolytungstic acids are $H_3W_{12}PO_{40}$, $H_4W_{12}SiO_{40}$, $H_3W_{12}VO_{40}$, $H_6W_6TeO_{24}$, $H_6W_{18}P_2O_{62}$, etc. Heteropolyacids obtained by replacing part of the condensed coordinating element, i.e., molybdenum and tungsten, with such an element as vanadium, such as $H_5Mo_{10}V_2PO_{40}$, $H_6W_9V_3PO_{40}$, etc., can be used in this invention. In addition, acidic salts obtained by replacing part of the proton of heteropolyacids with a metal ion, such as $HCs_3Mo_{12}SiO_{40}$, $HCuW_{1.2}PO_{40}$, etc., can be used in this invention.

The process of this invention can be carried out at a temperature of from 0° C. to 250° C., and preferably carried out at from about 20° C. to 150° C. The catalyst is suspended in a liquid phase or the liquid phase is passed through a fixed bed of the catalyst. When heteropolymolybdic acid, heteropolytungstic acid, or its acidic salt is used, the reaction can be carried out in a uniform liquid phase because they are strong acids and soluble in water or various organic solvents. If desired, the heteropolyacid is deposited on a suitable carrier, and the reaction can be carried out using a suspended bed or a fixed bed catalyst arrangement.

The amount of the catalyst used is not critical. When the reaction is carried out by suspending the catalyst in a liquid phase or carried out in a uniform liquid phase, it is used in an amount of from 0.1 to 500 mmoles, preferably from 1 to 100 mmoles, per mole of carbanilate, or 10 to 1,000 meq per mole of carbanilate. In the case of carrying out the reaction in a fixed bed catalyst, the flow rate of the starting material carbanilates is from about 0.1 to 100 moles/hr per liter of the catalyst.

When ethylcarbanilate, for example, is used as a starting material in the practice of this invention, the main products obtained are: 4,4'-methylenebis(ethylcarbanilate), represented by the formula (I):

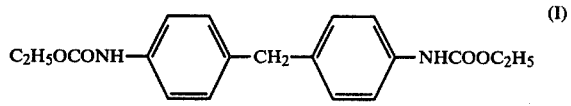

2,4'-methylenebis(ethylcarbanilate), represented by the formula (II):

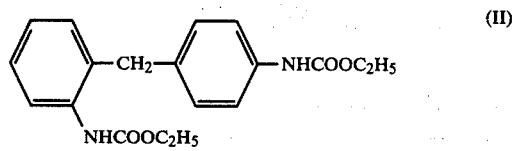

and dimers represented by the formulae (III), (IV) and (V):

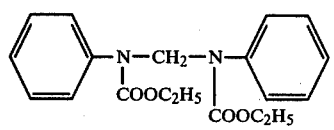

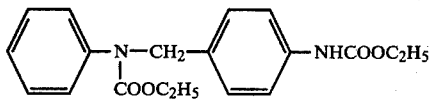

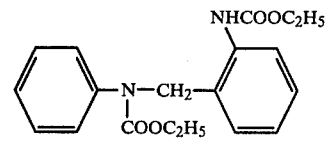

The dimers represented by the formulae (III), (IV) and (V) are all isomerized in the presence of an acid catalyst and converted into methylenebis(ethylcarbanilate) represented by the formulae (I) and (II). Therefore, by returning the dimers represented by the formulae (III), (IV) and (V) to the reaction system, the yield of methylenebis(ethylcarbanilate) can be further increased.

The following examples are given to illustrate this invention in greater detail.

EXAMPLE 1

A 100 ml glass reactor equipped with a stirrer and a reflux condenser was charged with 46.5 mmoles of ethylcarbanilate, 3.33 mmoles of trioxane, 30 ml of benzene and 5 ml of a cation exchanger containing sulfonic acid groups (Amberlyst 15, produced by Rohm & Haas Co.) and they were reacted with stirring for 270 minutes while refluxing at 84° C.

Gas chromatographic and high speed liquid chromatographic analyses of the reaction solution showed that the conversion of ethylcarbanilate was 32.3%, the amount of 2,4'-methylenebis(ethylcarbanilate) (hereinafter referred to as "2,4'-MDU") formed was 0.93 mmoles, and the amount of 4,4'-methylenebis(ethylcarbanilate) (hereinafter referred to as "4,4'-MDU") formed was 7.75 mmoles.

EXAMPLES 2 AND 6

The same reactor as used in Example 1 was charged with catalyst, starting materials, and solvent in the amounts as shown in Table 3, and they were reacted in an analogous manner as in Example 1 under the conditions as shown in Table 3. In the same manner as in Example 1, the reaction solution was analyzed. The results are shown in Table 4.

EXAMPLES 3 TO 5

A 100 ml glass reactor equipped with a stirrer and a circulating azeotropic dehydrating apparatus was charged with the catalyst, starting materials and solvent in the amounts as shown in Table 3, and they were reacted while dehydrating continuously under azeotropic conditions. In the same manner as in Example 1, the reaction solution was analyzed. The results are shown in Table 4.

EXAMPLES 7 TO 10, 12 TO 20

In the same reactor as used in Example 1 or Examples 3 to 5, the catalyst, starting materials and solvent in the amounts as shown in Table 3 were reacted under reflux conditions or while continuously dehydrating under azeotropic dehydrating conditions. These reaction conditions are shown in Table 3. The reaction solution was analyzed in the same manner as in Example 1. The results are shown in Table 4.

EXAMPLE 11

Through a glass reaction tube with an inner diameter of 10 mm which had been charged with 10 ml of Diaion HPK-25 and placed in an oil bath at 80° C., ethylcarbanilate, trioxane and benzene were passed at flow rates of 21.3 mmoles/hr, 1.41 mmoles/hr and 15 ml/hr, respectively. After 165 minutes from the start of the reaction, an effluent was taken out and analyzed. The conversion of ethylcarbanilate was 25.0%, and the yields of 2,4'-MDU and 4,4'-MDU were respectively 0.48 mmoles/hr and 4.42 mmoles/hr.

TABLE 3

| Example | Catalyst Type | Catalyst Amount (ml) | HCHO | Amount (mmoles) | Carbanilate | Amount (mmoles) | Solvent Type | Solvent Amount (ml) | Reaction Temperature (°C.) | Reaction Time (hrs) |
|---|---|---|---|---|---|---|---|---|---|---|
| 2 | Amberlite 200[3] | 5 | Trioxane | 3.33 | EPU[1] | 46.8 | Benzene | 30 | *84 | 4.5 |
| 3 | Nafion 501[4] | 2.4 g | " | 6.66 | " | 50 | Benzene Toluene | 10 20 | **101 | 6 |
| 4 | Diaion HPK-25[5] | 5 | " | 3.33 | " | " | Benzene | 30 | **85 | 2 |
| 5 | " | " | " | 6.66 | MPU[2] | 100 | Cyclohexane | 60 | ** | " |
| 6 | " | 2.5 | 37% Formalin | 0.81 g | EPU | 50 | Dioxane | 30 | *85 | 6 |
| 7 | " | 5 | Trioxane | 33.3 | " | 100 | Benzene | 60 | *77 | 3 |
| 8 | " | 2.5 | " | 1.67 | " | 50 | " | 30 | **85 | 6 |
| 9 | " | 1.3 | " | 3.33 | " | " | " | " | **86 | 1 |
| 10 | " | 10 | " | 8.3 | " | " | " | " | **83 | 5 |
| 12 | HPA[6] | 0.5 mmoles | " | 6.66 | " | " | Benzene Toluene | 10 20 | **101 | ¼ |
| 13 | " | 0.2 mmoles | " | 1.65 | " | 22.5 | Benzene | 15 | 31 | 7.5 |
| 14 | HPA[7] | 1.0 g | " | 3.33 | " | 47.5 | " | 30 | 83 | 5.5 |
| 15 | KSF/O[8] | 2.0 g | " | " | " | 46.8 | " | " | * | 2 |
| 16 | KSF/O[8] | 2.0 g | Trioxane | 8.52 | EPU | 51.1 | Benzene | 30 | * | 1 |
| 17 | " | " | " | 5.83 | " | 47.2 | " | " | * | 4 |
| 18 | " | " | 37% Formalin | 0.81 g | " | 48.4 | Dioxane | " | * | " |
| 19 | Zeolon 100[9] | " | Trioxane | 3.33 | " | 48.0 | Benzene | " | * | " |
| 20 | Silica[10] Titania | 5 | " | " | " | 50.0 | Toluene | " | *110 | 6 |

Note:
[1]Ethylcarbanilate
[2]Methylcarbanilate
[3]Cation exchanger containing sulfonic acid groups, produced by Rohm & Haas Co.
[4]Sulfonated perfluoroethylene resin, produced by Dupont Co.
[5]Cation exchanger containing sulfonic acid groups, produced by Mitsubishi Chemical Industries, Ltd.
[6]Phosphomolybdic acid ($H_3Mo_{12}PO_{40}$)
[7]Silicotungstic acid ($H_4W_{12}SiO_{40}$)
[8]Montmorillonite KSF/O, produced by Gardler Chemical Co.
[9]Synthetic zeolite, produced by Norton Co.
[10]Si/Ti = 1/6.93
*Under reflux conditions
**Under azotropic conditions

TABLE 4

| Example | Conversion of[1] Carbanilate (%) | Yield[2] (mmoles) 2,4'-MDU | Yield[2] (mmoles) 4,4'-MDU |
|---|---|---|---|
| 2 | 29.5 | 0.81 | 7.49 |
| 3 | 60.6 | 0.84 | 11.4 |
| 4 | 32.0 | 0.85 | 10.2 |
| 5 | 24.5 | 0.14[3] | 8.48[4] |
| 6 | 15.2 | 0.15 | 3.00 |
| 7 | 64.3 | | |
| 8 | 16.3 | | |
| 9 | 16.4 | | |
| 10 | 56.0 | | |
| 12 | 34.5 | 1.03 | 12.69 |
| 13 | 26.5 | 0.19 | 2.73 |
| 14 | 6.9 | 0.06 | 0.54 |
| 15 | 34.4 | 0.40 | 14.2 |
| 16 | 51.0 | 0.23 | 3.74 |
| 17 | 57.6 | 0.81 | 13.8 |
| 18 | 9.3 | 0.03 | 0.35 |
| 19 | 1.2 | 0.05 | 0.18 |
| 20 | 5.0 | | 0.44 |

Note:
$\frac{\text{Reacted carbanilate}}{\text{Fed carbanilate}} \times 100$ (the conversion of carbanilate in Examples 1, 11 and 21 was obtained in this manner)
[2]The yield was calculated based on the results of high speed liquid chromatographic analysis using:
apparatus: duPont's 830 type
column: Zonbax Sil, 4.6 φ × 250 mm
carrier: Chloroform, 0.8 ml/min, 700 psig
internal standard: diethyl phthalate
detector: UV 254 mm
In the analysis, the peak size of each component against the peak of internal standard on the chromatogram was indicated as an area ratio, and the absolute amount of each component was calculated according to the following expression, for which the calibration factor was previously calculated with respect to the internal standard.
Amount (produced) of component A =
$\frac{\text{peak area of component A}}{\text{peak area of internal standard}} \times$ used amount of internal standard × calibration factor
(The yield of the reaction product in Examples 1, 11 and 21 were obtained by the above-mentioned manner.)
[3]2,4'-methylenebis (methylcarbanilate)
[4]4,4'-methylenebis (methylcarbanilate)

EXAMPLE 21

Through a glass reaction tube with an inner diameter of 10 mm which had been charged with 10 ml of Montomorillonite KSF/O (produced by Gardler Chemical Co.) and placed in an oil bath at 86° C. was passed at a flow rate of 2.5 ml per hour a solution prepared by mixing in a ratio of 51 mmoles of ethylcarbanilate, 3.33 mmoles of trioxane and 30 ml of toluene. After 210 minutes from the start of the reaction, an effluent was taken out and analyzed. The conversion of ethylcarbanilate was 35.5%, and 2,4'-MDU and 4,4'-MDU were produced in 0.033 mmoles/hr and 0.732 mmoles/hr, respectively.

EXAMPLES 22 TO 35

In a 200 ml three necked flask equipped with a thermometer, refluxcondenser and a stirrer, ethylcarbanilate, trioxane (or a 35% aqueous solution of formaldehyde) and a solvent were placed, in the amounts shown in Table 5, and additionally 5 ml of the catalyst as shown in Table 5 was added thereto. They were reacted at 80° C. for a predetermined period of time (see Table 5) in an oil bath.

By analyzing the solution formed by high speed liquid chromatography, the conversion of ethylcarbanilate, and the yields of methylenebis(ethylcarbanilate) (hereinafter referred to as "MDU"), and 4,4'-MDU were determined. The results are shown in Table 6.

TABLE 5

| Example | Catalyst | EPC[1] (mmoles) | HCHO[2] (mmoles) | Solvent Type | Amount (ml) | Reaction Time (hrs) |
|---|---|---|---|---|---|---|
| 22 | Diaion HPK 25 | 50.12 | 10.02[3] | Acetic Acid | 30 | 4 |
| 23 | Diaion HPK 40 | 50.32 | 10.06[3] | " | " | 2 |
| 24 | " | 50.12 | 10.02[3] | Toluene | 60 | 2 |
| 25 | " | 50.28 | 10.06[3] | Chlorobenzene | 30 | 4 |
| 26 | Diaion HPK 55 | 50.45 | 10.09[3] | Acetic Acid | " | 4 |
| 27 | " | 50.03 | 10.01[3] | Chlorobenzene | " | 4 |
| 28 | " | 50.45 | 10.09[3] | Toluene | 60 | 3 |
| 29 | Montmorillonite KSF/O | 50.03 | 10.01[3] | Acetic Acid | 30 | 8 |
| 30 | Montmorillonite KSF/O | 50.02 | 10.00[3] | " | " | 4 |
| 31 | Montmorillonite KSF/O | 50.03 | 10.01[3] | Acetic Acid Chlorobenzene | 30 | 8 |
| 32 | Montmorillonite KSF/O | 50.15 | 10.03[3] | Toluene | 60 | 2 |
| 33 | Diaion HPK 40 | 51.61 | 10.32[4] | Acetic Acid | 30 | 4 |
| 34 | Diaion HPK 55 | 50.78 | 10.15[4] | Toluene | " | 9 |
| 35 | Montmorillonite KSF/O | 48.40 | 10.00[3] | Dioxane | " | 4 |

Notes:
[1]Ethylcarbanilate
[2]Trioxane and a 35% by weight aqueous solution of formaldehyde were converted to and are indicated on a formaldehyde basis.
[3]As trioxane.
[4]As a 35% by weight aqueous solution of formaldehyde.

TABLE 6

| Example | Conversion of[1] EPC (%) | Yield[2] (%) Dimer[3] | MDU | 4,4'-MDU |
|---|---|---|---|---|
| 22 | 80.8 | — | 56.1 | 52.2 |
| 23 | 100.5 | 60.8 | 49.4 | 46.5 |
| 24 | 67.7 | 48.1 | 39.0 | 35.7 |
| 25 | 83.8 | 53.0 | 50.3 | 46.3 |
| 26 | 94.7 | — | 64.6 | 61.0 |
| 27 | 96.1 | — | 48.0 | 44.7 |
| 28 | 76.8 | 52.8 | 47.3 | 44.0 |
| 29 | 89.8 | 87.3 | 44.0 | 41.5 |
| 30 | 81.4 | 84.6 | 22.1 | 20.8 |
| 31 | 82.0 | 77.8 | 31.1 | 29.7 |
| 32 | 40.1 | 28.8 | 22.5 | 21.9 |
| 33 | 84.7 | 84.2 | 43.1 | 40.6 |
| 34 | 61.6 | 56.2 | 37.0 | 34.8 |
| 35 | 22.5 | 8.3 | 3.8 | 3.5 |

Note:
[1]Conversion of ethylcarbanilate (based on formaldehyde)

$$\frac{\text{Reacted ethylcarbanilate (moles)} \times \frac{1}{2}}{\text{Fed formaldehyde (moles)}} \times 100$$

[2]Yield (based on formaldehyde)
The yield was calculated based on the results of the high speed liquid chromatographic analysis using:
apparatus: Hitachi pump control unit 635 Type and Shimadzu SPD-1 type detector
column: Zonbax Sil 4.6$\phi$ × 250 mm
carrier: n-hexane/chloroform (40/60 vol. %) 1.5 ml/min., 1035 psig
internal standard: 4,4'-methylenebis(methylcarbanilate)
detector: UV 254 mm
In the analysis, the peak size of each component against the peak of internal standard on the chromatogram was indicated as an area ratio, and the absolute amount of each component was calculated according to the following expression, for which the calibration factor was previously calculated with respect to the internal standard.
amount (produced) of component A =
$\frac{\text{peak area of component A}}{\text{peak area of internal standard}} \times$
used amount of internal standard × calibration factor yield of MDU (%) =
$\frac{2,4'\text{-MDU (produced)} + 4,4'\text{-MDU (produced)}}{\text{HCHO (fed)}} \times 100$ yield of 4,4'-MDU (%) =
$\frac{4,4'\text{-MDU (produced)}}{\text{HCHO (fed)}} \times 100$

[3]Accumulated yield of compounds represented by the formulae (I), (II), (III), (IV) and (V).

EXAMPLES 36 TO 44

In a 200 ml three necked flask equipped with a thermometer, reflux condenser, and a stirrer, ethylcarbanilate, formaldehyde compound, 30 ml of a solvent and a catalyst were placed, and then reacted at a predetermined temperature on an oil bath for a predetermined period of time. By analyzing the solution formed by high speed liquid chromatography, the conversion of ethylcarbanilate, and the yields of dimer, MDU and 4,4'-MDU were determined.

The amounts of ethylcarbanilate and formaldehyde used, the type of the solvent, the reaction temperature, the type and amount of the catalyst, and the reaction time are shown in Table 7. The results are shown in Table 8.

TABLE 8

| Example | Conversion of[1] EPC (%) | Yield[2] (%) Dimer[3] | MDU | 4,4'-MDU |
|---|---|---|---|---|
| 36 | 99.5 | 68.1 | 68.1 | 64.4 |
| 37 | 89.1 | 58.4 | 58.4 | 55.4 |
| 38 | 88.4 | 56.2 | 20.9 | 20.3 |
| 39 | 89.0 | 72.0 | 55.8 | 53.1 |
| 40 | 91.5 | 60.4 | 60.4 | 57.5 |
| 41 | 61.6 | 60.0 | 1.9 | 1.9 |
| 42 | 85.6 | 66.1 | 66.1 | 62.7 |
| 43 | 16.4 | — | — | — |
| 44 | 66.3 | 41.5 | 19.2 | 18.1 |

Note:
[1], [2], [3] Same as defined in Table 6.

EXAMPLES 45 TO 65

In the same reactor as used in Examples 22 to 35 ethylcarbanilate, formaldehyde compound, a catalyst and a solvent were placed in predetermined amounts, and were reacted at 80° C. on an oil bath for a predetermined time, as shown in Table 9. By analyzing the solution formed by high speed liquid chromatography, the conversion of ethylcarbanilate and the yields of dimer, the MDU and 4,4'-MDU were determined. The results are shown in Table 10.

TABLE 9

| Example | Catalyst Type | Amount (mmoles) | EPU[1] (mmoles) | HCHO[2] (mmoles) | Solvent Type | Amount (g) | Reaction Time (hrs) |
|---|---|---|---|---|---|---|---|
| 45 | H4Mo12PO40 | 0.10 | 101.37 | 10.72[3] | CH3COOH | 30 | 4.0 |
| 46 | " | " | 203.59 | 10.76[3] | " | " | " |
| 47 | " | " | 50.97 | 10.77[3] | CH3NO2 | " | " |
| 48 | H4W12PO40 | " | 51.34 | 10.86[3] | " | " | " |
| 49 | " | " | 50.60 | 10.12[4] | CH3CN | " | 2.0 |
| 50 | " | " | 53.38 | 11.29[3] | ClCH2CH2Cl | " | " |
| 51 | " | " | 49.63 | 10.49[3] | Sulfolane[10] | " | " |
| 52 | " | " | 50.95 | 10.77[3] | o-dichlorobenzene | " | " |
| 53 | " | " | 51.03 | 10.79[3] | cyanobenzene | " | " |
| 54 | " | " | 49.99 | 10.57[3] | dinitrotoluene | " | " |
| 55 | " | " | 50.76 | 10.73[3] | p-nitrotoluene | " | " |
| 56 | " | " | 50.04 | 10.01[4] | nitrobenzene | " | " |
| 57 | " | " | 100.67 | 10.65[3] | " | " | " |
| 58 | " | " | 204.57 | 10.81[3] | " | " | " |
| 59 | " | " | 51.02 | 10.20[5] | " | " | " |
| 60 | H4W12PO40 | 0.10 | 51.14 | 10.29[6] | nitrobenzene | 30 | 2.0 |
| 61 | H4W12SiO40 | " | 51.46 | 10.88[3] | " | " | " |
| 62 | HPK-40[7] | 5 ml | 50.60 | 10.12[5] | CH3COOH | " | 4.0 |
| 63 | PK-228[8] | " | 51.31 | 10.85[3] | " | " | " |
| 64 | KSF/O[9] | 2.02 g | 50.17 | 10.03[4] | nitrobenzene | " | 2.0 |
| 65 | H4W12PO40 | 0.10 | 101.20 | 5.35[3] | " | 60 | " |

Note:
[1] Ethylcarbanilate
[2] Converted to a formaldehyde basis.
[3] A 37% by weight aqueous solution of formaldehyde.
[4] Trioxane
[5] CH2(OCOCH3)2
[6] CH2(OC2H5)2
[7] Cation exchanger containing sulfonic acid groups: trade name Diaion HPK-40, produced by Mitsubishi Chemical Industries Ltd.
[8] Cation exchanger containing sulfonic acid groups: trade name Diaion PK-228, produced by Mitsubishi Chemical Industries Ltd.
[9] Montmorillonite KSF/O, produced by Gardler Chemical Co.
[10] Tetrahydrothiophene-1,1-dioxide

TABLE 10

| Example | Conversion of[1] EPC (%) | Yield[2] (%) Dimer[3] | MDU | 4,4'-MDU |
|---|---|---|---|---|
| 45 | 19.0 | 92.4 | 78.1 | 67.7 |
| 46 | 9.1 | 97.8 | 79.1 | 68.2 |
| 47 | 37.5 | 76.8 | 66.3 | 59.4 |
| 48 | 37.5 | 80.6 | 71.9 | 64.3 |
| 49 | 32.6 | 65.2 | 53.3 | 48.6 |
| 50 | 39.2 | 74.2 | 57.2 | 48.6 |
| 51 | 38.5 | 68.4 | 46.0 | 40.1 |
| 52 | 37.9 | 72.9 | 60.5 | 50.6 |
| 53 | 34.7 | 65.5 | 34.7 | 30.7 |
| 54 | 42.4 | 85.4 | 77.3 | 67.9 |
| 55 | 40.9 | 79.5 | 71.6 | 62.5 |
| 56 | 39.7 | 79.6 | 73.5 | 64.0 |
| 57 | 24.0 | 93.0 | 82.4 | 72.0 |
| 58 | 11.7 | 98.1 | 83.9 | 72.7 |
| 59 | 24.9 | 57.1 | 54.0 | 46.3 |
| 60 | 37.3 | 74.9 | 67.8 | 59.2 |
| 61 | 41.1 | 78.0 | 65.7 | 56.7 |
| 62 | 28.4 | 58.6 | 51.7 | 43.8 |
| 63 | 29.1 | 63.3 | 24.0 | 20.3 |
| 64 | 41.1 | 73.1 | 63.6 | 57.3 |
| 65 | 5.5 | 98.7 | 89.0 | 78.3 |

Note:
[1] Conversion of ethylcarbanilate
$$\frac{\text{Reacted ethylcarbanilate}}{\text{Fed ethylcarbanilate}} \times 100$$
[2] Same as defined in Table 6.
[3] Same as defined in Table 6.

What is claimed is:

1. A process for producing a methylenedicarbanilate which comprises reacting a carbanilate with formaldehyde compound in the presence of at least one catalyst selected from the group consisting of:
   (1) heteropolymolybdic acid; and
   (2) heteropolytungstic acid.

2. A process as in claim 1 wherein the carbanilate is represented by the formula

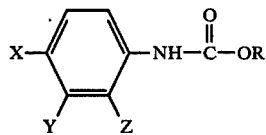

wherein R is an alkyl group containing from 1 to 4 carbon atoms or a phenyl group, and X, Y and Z are each hydrogen, a halogen atom, a nitro group, an alkyl group containing from 1 to 5 carbon atoms, an alkoxy group containing from 1 to 5 carbon atoms, or an alkoxy carbamoylphenylmethyl group wherein the alkoxy portion contains from 1 to 4 carbon atoms.

3. A process as in claim 1 wherein the carbanilate is a member selected from the group consisting of methylcarbanilate, ethylcarbanilate, phenylcarbanilate, 2,4'-methylenebis(ethylcarbanilate) and 4,4'-methylenebis(ethylcarbanilate).

4. A process as in claim 1 wherein the formaldehyde compound is at least one member selected from the group consisting of gaseous formaldehyde, an aqueous solution of formaldehyde, trioxane, paraformaldehyde, acetals of formaldehyde, acylals of formaldehyde and oxymethylenebiscarboxylates.

5. A process as in claim 1 wherein the carbanilate is used in an amount of at least 2 moles per mole of formaldehyde compounds, converted to a formaldehyde basis.

6. A process as in claim 1 wherein the carbanilate is used in an amount of from 3 to 10 moles per mole of formaldehyde compounds, converted to a formaldehyde basis.

7. A process as in claim 1 wherein the process is carried out by suspending the catalyst in a liquid phase or carried out in a uniform liquid phase and the acid catalyst is used in an amount of from 0.1 to 500 mmoles per mole of the carbanilate.

8. A process as in claim 7 wherein the acid catalyst is used in an amount of from 1 to 100 moles per mole of the carbanilate.

9. A process as in claim 1 wherein the process is carried out using a fixed bed catalyst and wherein the carbanilate is supplied to the reaction at a rate of from about 0.1 to 100 moles/hr per liter of the catalyst.

10. A process as in claim 1 wherein the reaction is carried out in the presence of a solvent.

11. A process as in claim 10 wherein at least one component of the solvent is a member selected from the group consisting of aliphatic carboxylic acids, nitroalkanes, aromatic nitro compounds, halogenated alkanes, aromatic halides, nitriles, and cyclic sulfones.

12. A process as in claim 1, wherein said heteropolymolybdic acid is $H_3Mo_{12}PO_{40}$, $H_4Mo_{12}TiO_{40}$, $H_8Mo_{12}CeO_{42}$, $H_8Mo_{11}GeO_{39}$, $H_6Mo_9MnO_{32}$, $H_5Mo_6IO_{24}$, $H_9Mo_6CrO_{24}$, $H_6Mo_{18}As_2O_{62}$, $H_5Mo_{10}V_2PO_{40}$, $H_6W_9V_3PO_{40}$, or $HCs_3Mo_{12}SiO_{40}$.

13. A process as in claim 1, wherein said heteropolytungstic acid is $H_3W_{12}PO_{40}$, $H_4W_{12}SiO_{40}$, $H_3W_{12}VO_{40}$, $H_6W_6TeO_{24}$, $H_6W_{18}P_2O_{62}$, $H_6W_9V_3PO_{40}$, or $HCuW_{12}PO_{40}$.

* * * * *